United States Patent [19]

Curran et al.

[11] 4,399,132

[45] Aug. 16, 1983

[54] 7-BETA-[ALPHA-SYN-METHOXYIMINO-ALPHA-(2-AMINOTHIAZOL-4-YL)-ACETAMIDO]-3-[(1,2,3-THIADIAZOL-5-YLTHIO)METHYL]-3-CEPHEM-4-CARBOXYLIC ACID AND $C_1$–$C_6$ ALKYL DERIVATIVES THEREOF

[75] Inventors: William V. Curran, Pearl River; Adma S. Ross, Suffern, both of N.Y.

[73] Assignee: American Cyanamid Company, Stamford, Conn.

[21] Appl. No.: 281,438

[22] Filed: Jul. 8, 1981

Related U.S. Application Data

[63] Continuation-in-part of Ser. No. 176,889, Aug. 11, 1980, abandoned.

[51] Int. Cl.³ .................. A61K 31/545; C07D 501/56
[52] U.S. Cl. ........................... 424/246; 544/27
[58] Field of Search ......................... 544/27; 424/246

[56] References Cited

U.S. PATENT DOCUMENTS

| | | | |
|---|---|---|---|
| 4,098,888 | 7/1978 | Ochiai et al. | 544/27 |
| 4,278,671 | 7/1981 | Ochiai et al. | 544/25 |
| 4,278,793 | 7/1981 | Durckheimer | 544/27 |

*Primary Examiner*—Paul M. Coughlan, Jr.
*Attorney, Agent, or Firm*—Mary-Ellen M. Timbers; Robert P. Raymond

[57] ABSTRACT

7-Beta-[alpha-syn-methoxyimino-alpha-(2-aminothiazol-4-yl)acetamido]-3-[(1,2,3-thiadiazol-5-ylthio)methyl]-3-cephem-4-carboxylic acid and $C_1$–$C_6$ alkyl derivatives thereof, useful as antibacterial agents.

9 Claims, No Drawings

7-BETA-[ALPHA-SYN-METHOXYIMINO-ALPHA-(2-AMINOTHIAZOL-4-YL)-ACETAMIDO]-3-[(1,2,3-THIADIAZOL-5-YLTHIO)METHYL]-3-CEPHEM-4-CARBOXYLIC ACID AND C₁-C₆ ALKYL DERIVATIVES THEREOF

CROSS-REFERENCE TO RELATED APPLICATIONS

This application is a continuation-in-part of application Ser. No. 176,889, filed Aug. 11, 1980, now abandoned.

BACKGROUND OF THE INVENTION

1. Field of Invention

This invention relates to cephalosporanic acids, esters, and acid salts. More particularly, this invention relates to cephalosporanic compounds having at the 7-position the 2-aminothiazol syn-methoxyimino acetamido moiety and at the 3-position the 1,2,3-thiadiazol thiomethyl group, optionally substituted with $C_1$-$C_6$ alkyl.

2. Description of the Prior Art

South African Pat. Nos. 757892, 772030, and 781870 generically disclose cephalosporin compounds which may have at the 7-position the 2-aminothiazol-4-yl syn-methoxyimino acetamido moiety, and at the 3-position a 1,2,3-thiadiazol-5-yl thiomethyl group. However, as all of these patents contain very broad generic disclosures and none of these patents specifically names or describes the compounds of the present invention, they are non-anticipatory of the selective invention disclosed and claimed herein.

SUMMARY OF THE INVENTION

This invention is concerned with cephalosporin derivatives of the formula:

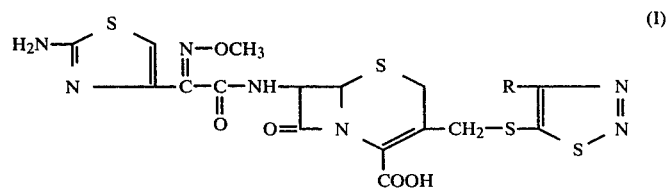

wherein R is hydrogen or $R_1$, $R_1$ being $C_1$-$C_6$ alkyl, and the pharmaceutically acceptable nontoxic salts thereof. These compounds are antibacterial agents active against both Gram-positive and Gram-negative bacteria.

The present invention further encompasses compositions of matter containing said compounds and methods of using said compounds.

DESCRIPTION OF THE PREFERRED EMBODIMENTS

The compounds of the present invention may be divided into two subgenera:

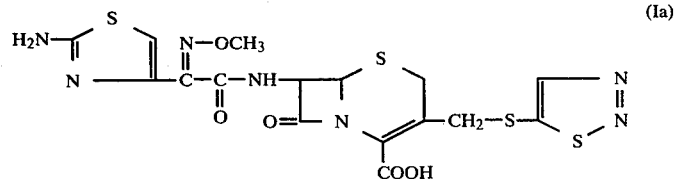

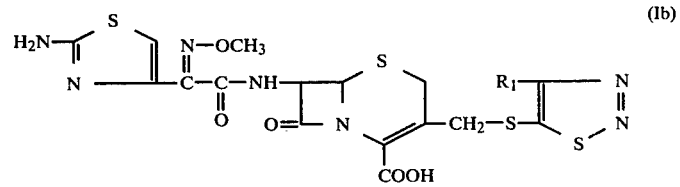

wherein $R_1$ is $C_1$-$C_6$ alkyl.

One preferred embodiment is represented by Formula Ib wherein $R_1$ is $C_1$-$C_6$ alkyl.

A more preferred embodiment is represented by Formula Ib wherein $R_1$ is methyl.

The most preferred embodiment is represented by Formula Ia.

The novel compounds of this invention may be prepared in the free acid form according to Flowcharts A, B, or C:

FLOWCHART A

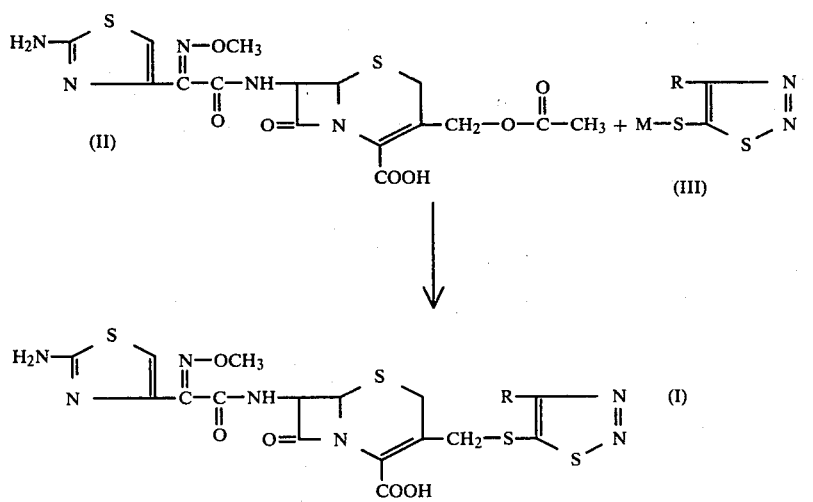

Compound II, 7-beta-[alpha-syn-methoxyimino-alpha-(2-aminothiazol-4-yl)acetamido-3-(acetoxymethyl)-3-cephem-4-carboxylic acid, also called Cefotaxime, is prepared by the method of South African Pat. No. 7801870.

Compound III, 1,2,3-thiadiazole-5-thiol, wherein R is hydrogen or $R_1$ and $R_1$ is $C_1$-$C_6$ alkyl, and M is hydrogen or an alkali metal cation, is prepared according to the method of P. Demaree, M. Doria, and J. Muchowski, "Five-Membered Heterocyclic Thiones, Part VII (1,2): 1,2,3-Thiadiazole-5-thiolates,"J. Hetero. Chem. 15: 1295 (1978). As used hereinabove and below, the term "$C_1$-$C_6$ alkyl" refers to a straight- or branched-chain, monovalent substituent consisting solely of carbon and hydrogen, containing no unsaturation, and having 1 to 6 carbon atoms. Examples of such alkyl groups are methyl, ethyl, n-propyl, isopropyl, n-butyl, t-butyl, n-hexyl, 2-methylpentyl and the like. Examples of suitable alkali metal cations for M are sodium and potassium.

In accordance with Flowchart A, the cephalosporin compound II is treated with thiadiazole compound III in a polar solvent at about pH 6-7.5, preferably about 7-7.5, at about 40°-70° C. (preferably about 65° C.) for approximately 4-12 hours, preferably about 6-12 hours. The reaction mixture is then cooled and acidified to about pH 2.5-3.0, and the resulting product is collected by conventional means.

A wide variety of polar solvents are used for the reaction mixture, such as for example acetonitrile, dimethyl formamide, dimethyl sulfoxide, tetrahydrofuran, lower alkyl alcohols, ethoxylated ethers such as diglyme, lower alkyl phthalates, lower alkyl ketones, etc. Preferably these are diethyl ether, acetone, ethyl alcohol, and mixtures thereof. More preferably they are aqueous mixtures of ethyl alcohol and acetone. Specifically preferred as a solvent is water.

The reaction is run at any pH between 6 and 7.5, but extreme acidity or basicity destroys the β-lactam ring and results in undesirable products. A preferred pH range is 7-7.5. The reaction will proceed at any temperature between approximately 40° and 70° C., but a temperature of 65° C. is preferred. While the reaction is most conveniently run at 1 ATM pressure, it is possible to proceed under pressure or vacuum as well. The reaction mixture may be heated for 4-12 hours, but 6-12 hours is preferred.

At the end of the reaction time the reaction mixture is cooled and acidified, preferably to pH 2.5-3.0. A lower pH is not recommended because the amino heterocyclo will tend to redissolve, and a higher pH is not effective to precipitate out the desired end product. Any dilute mineral acid such as sulfuric or hydrochloric acid is used to acidify the reaction mixture, but 1 N hydrochloric acid is preferred.

The end product is collected by any conventional means, such as for example by filtration, chromatography, etc.

Optionally, the amino group on the thiazol group may be protected during the above reaction sequence by an easily removable amino-protective group selected from those well-known to persons skilled in the art of peptide chemistry, e.g., trityl, benzyl, benzhydryl, chloroacetyl, trichloroacetyl, etc. See also South African Pat. Nos. 7801870 and 757892. In the event that the amino group is so protected, the product isolated above must be treated with an appropriate agent to remove the protecting group, yielding the desired product of Formula I.

FLOWCHART B

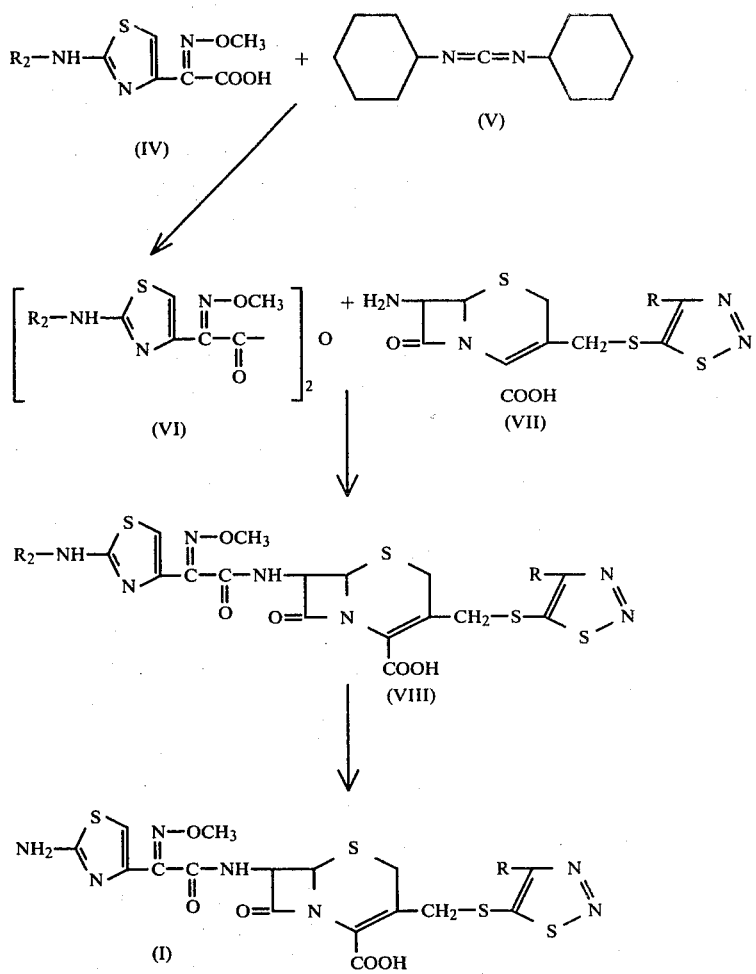

Compound IV, 2-(2-R₂amino-4-thiazolyl)-2-syn-methoxyiminoacetic acid wherein $R_2$ is an easily removable aminoprotective group well-known to those skilled in the art, is prepared by the method of Belgian Patent 850,662, or South African Pat. Nos. 7703775, 772030, and 7507892. Examples of suitable amino-protective groups are those usually employed in peptide chemistry such as alkylcarbonyl, e.g. formyl, acetyl, propionyl; alkoxycarbonyl, e.g. t-butoxycarbonyl; alkoxyalkylcarbonyl, e.g. methoxyacetyl, methoxypropionyl; substituted alkoxycarbonyl, e.g. trichloroethoxycarbonyl; aralkoxycarbonyl, e.g. benzyloxycarbonyl; substituted aralkoxycarbonyl, e.g. p-nitrobenzyloxycarbonyl; and trityl. Trityl is preferred.

Compound VII, 7-amino-3-(1,2,3-thiadiazol-5-yl) thiomethyl-3-cephem-4-carboxylic acid wherein R is hydrogen or $R_1$, $R_1$ being $C_1-C_6$ alkyl, is prepared by the method of G. S. Lewis and P. H. Nelson, "3-[1,2,3-Thiadiazol-5-ylthio) methyl]cephalosporins", J. Med. Chem 22(10): 1214 (1979).

In accordance with Flowchart B, Compound IV is reacted with dicyclohexylcarbodiimide (Compound V) in a solvent such as methylene chloride, chloroform, or ethyl acetate with stirring at 0°–5° C. for 15–45 minutes and then at ambient temperature for 1–2 hours followed by filtration. The filtrate containing Compound VI (wherein $R_2$ is as defined above) is chilled in an ice/methanol bath and reacted with a cold solution of Compound VII (wherein R is as defined above) and triethylamine in the same solvent as above. This mixture is stirred at 0°–5° C. for 15–45 minutes and then at ambient temperature overnight. The reaction mixture is extracted is succession with cold dilute mineral acid, cold water, cold brine, and dried. Evaporation of the solvent gives an oil which is dissolved in a 1:1 mixture of dioxane and ether; diethylamine is added and the solution is chilled and filtered, giving the diethylammonium salt of 2-(2-R₂amino-4-thiazolyl)-2-syn-methoxyiminoacetic acid as a by-product. The filtrate is diluted with ether, chilled, and filtered, giving 7-[2-(2-R₂amino-4-thiazolyl)-2-syn-methoxyiminoacetamido]-3-(1,2,3-thiadiazol-5-yl)thiomethyl-3-cephem-4-carboxylic acid (Compound VIII, wherein R and $R_2$ are as defined above) as the diethylammonium salt.

This salt is reacted with an appropriate agent chosen to remove the particular $R_2$-protecting group employed. These agents are well-known to those skilled in the art. When $R_2$ is trityl, treatment with 80% formic acid at ambient temperature for 1–4 hours is preferred. The reaction mixture is then diluted with water and filtered. The filtrate is evaporated at 25°–35° C. and the product precipitated from ether giving the desired product of Formula I.

FLOWCHART C

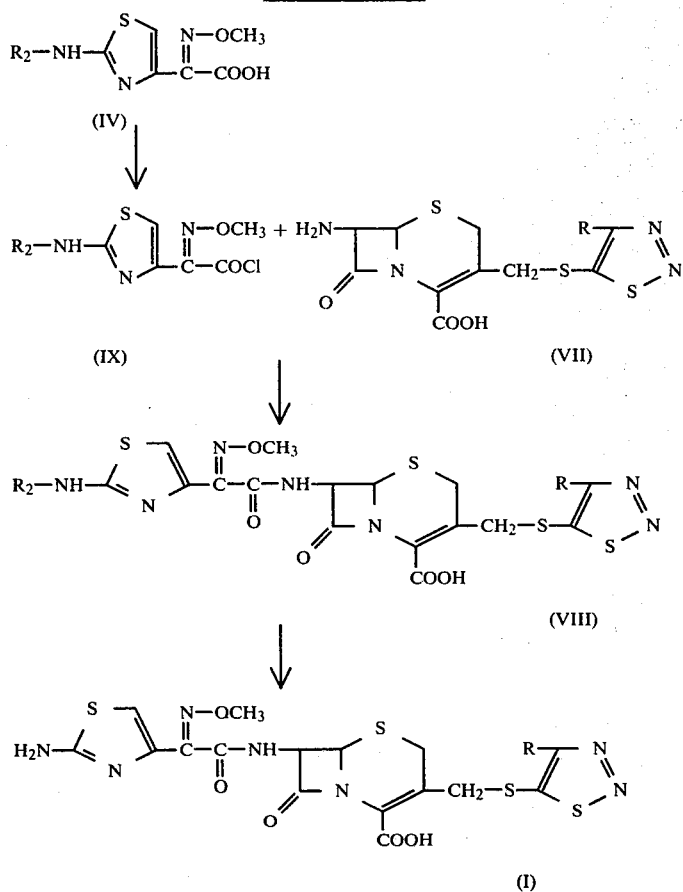

According to Flowchart C, Compound IV as defined above is converted to 2-(2-$R_2$-amino-4-thiazolyl)-2-syn-methoxyiminocarbonyl chloride (Compound IX) as follows: Compound IV and one molar equivalent of a tertiary organic amine (preferably triethylamine) are dissolved in a non-hydroxylic organic solvent (e.g. methylene chloride, chloroform, carbon tetrachloride; methylene chloride or chloroform is preferred) and chilled. To this cold stirred mixture phosphorous pentachloride is added in several portions over 15–30 minutes and the reaction mixture is stirred at 0°–5° C. for an additional 15–45 minutes, followed by stirring for about 1 hour at room temperature. The reaction mixture is then evaporated at reduced pressure, redissolved in chloroform or methylene chloride, and reevaporated. The residue is taken up in acetone and filtered, yielding the crystalline triethylammonium hydrochloride byproduct which is discarded.

The acetone filtrate containing Compound IX (wherein $R_2$ is as defined above) is added over about 30 minutes to a stirred ice-cold solution of the 7-aminocephalosporanic acid-thioheterocyclo (Compound VII, as defined above) in water:acetone (3:2 v/v) containing 1 molar equivalent of a weak base such as sodium bicarbonate and 2 molar equivalents of an organic tertiary amine, preferably triethylamine. This reaction mixture is stirred at room temperature for about one hour, acidified to ph 2 with dilute aqueous acid (e.g. 4 N hydrochloride), diluted with water, extracted repeatedly with an organic solvent such as methylene chloride, chloroform, ethyl acetate, benzene etc. (ethyl acetate is preferred), washed repeatedly with water, dried, and evaporated to yield the product of Formula VIII (as defined above).

Treatment with a suitable agent to remove the particular $R_2$-protecting group employed yields the desired product of Formula I.

The product of Formula I prepared by Flowchart A, B, or C may be converted to a pharmaceutically acceptable ester or salt by treatment with the appropriate alcohol or base. The term "pharmaceutically acceptable nontoxic esters or salts" refers to those esters or salts of the parent compound which do not significantly adversely affect the pharmaceutical properties (e.g. toxicity, effectiveness, etc.) of the parent compound such as are conventionally used in the pharmaceutical art. Preferred esters are pivaloyloxymethyl, methoxymethyl, phthalidyl, benzamidomethyl, 1'-ethoxycarbonyloxymethyl. The salts of the present invention are pharmaceutically acceptable cation salts with respect to the acid moiety. The alkali metal cations, e.g. sodium and potassium, are preferred. Particularly preferred is the sodium salt. For the purposes of this invention it is to be understood that the compounds of Formula I are equivalent to their pharmaceutically acceptable nontoxic cation salts.

It is generally preferred that the respective product of each process step, described above in Flowchart A, B, or C, is separated and/or isolated prior to its use as starting material for subsequent steps. Separation and isolation can be effected by any suitable purification procedure such as, for example, evaporation, crystallization, column chromatography, thin-layer chromatography, distillation, etc. Specific illustrations of typical separations and isolation procedures can be had by reference to the appropriate examples described hereinbelow; however, other equivalent separation procedures could, of course, also be used. Also, it should be appreciated that where typical reaction conditions (e.g. temperatures, mole ratios, reaction times) have been given above that conditions both above and below these ranges can also be used, though generally less conveniently.

The compounds of the present invention are biologically active and possess potent antibacterial activity when tested by the Mueller-Hinton agar dilution method. The results appear in Tables I, II, and III.

In Table I the compounds are coded as follows:
Compound Ia = 7 beta-[alpha-syn-methoxyamino-alpha-(2-aminothiazol-4-yl)acetamido]-3-[(1,2,3-thiadiazol-5-ylthio)methyl]-3-cephem-4-carboxylic acid
Compound II = Cephalothin (Lilly)

TABLE I

| | | Minimal Inhibitory Concentration mcg/ml Compound | |
|---|---|---|---|
| Organism | | Ia | II |
| GRAM-NEGATIVE | | | |
| Klebsiella pneumoniae | STFD-79-16 | .015 | 1 |
| Klebsiella pneumoniae | SSC-78-1 | .015 | 1 |
| Klebsiella oxytoca | K-81-6 | .03 | 2 |
| Enterobacter aerogenes | STFD-79-14 | .03 | 128 |
| Enterobacter cloacae | K-79-16 | .25 | >128 |
| Enterobacter cloacae | K-81-46 | .12 | 64 |
| Serratia marcescens | TUL-78-15 | 1 | >128 |
| Serratia marcescens | QHC-77-2 | 1 | >128 |
| Serratia marcescens | K-81-39 | .12 | >128 |
| Proteus morganii | K-79-25 | .015 | >128 |
| Proteus morganii | K-77-3 | 4 | >128 |
| Proteus rettgeri | N-76-1 | .015 | >128 |
| Providencia stuartti | K-81-29 | .06 | >128 |
| Escherichia coli | STFD-79-20 | .015 | 4 |
| Escherichia coli | #311 | .03 | 4 |
| Escherichia coli | K-81-14 | .06 | 64 |
| Salmonella sp. | SSC-79-57 | .25 | 64 |
| Salmonella (arizona) | QHC-77-3 | .03 | 2 |
| Citrobacter sp. | K-81-27 | .03 | 1 |
| Acinetobacter sp. | STFD-79-17 | 16 | >128 |
| Acinetobacter sp. | K-77-1 | 4 | >128 |
| Acinetobacter sp. | K-77-6 | 16 | >128 |
| Acinetobacter sp. Pseudomonas aeruginosa | SSC-78-13 | 64 | >128 |
| Pseudomonas aeruginosa | 12-4-4 | 32 | >128 |
| Pseudomonas aeruginosa | TUL-78-2 | 128 | >128 |
| GRAM-POSITIVE | | | |
| Enterococcus sp. | OSU-75-1 | 32 | 32 |
| Enterococcus sp. | SM-77-15 | 32 | 32 |
| Staphylococcus aureus | SSC-79-18 | .25 | .25 |
| Staphylococcus aureus | FU-79-19-2 | .5 | .5 |
| Staphylococcus aureus | SSC-80-15 | .5 | .5 |
| Staphylococcus aureus | Smith | .25 | .12 |

In Table II the Compounds are coded as follows:
Compound Ia = 7 beta-[alpha-syn-methoxyimino-alpha-(2-aminothiazol-4-yl)acetamido]-3-[1,2,3-thiadiazol-5-ylthio)methyl]-3-cephem-4-carboxylic acid
Compound II = Cefotaxime (Hoechst)
Compound III = Cefmenoxime (Takeda)
Compound IV = Ceftizoxime (Fujisawa)
Compound V = Moxalactam (Lilly)
Compound VI = Cefoxitin (Merck)
Compound VII = Cefaperazone (Pfizer)

TABLE II

| | Minimal Inhibitory Concentration, mcg/ml Compound | | | | | | |
|---|---|---|---|---|---|---|---|
| Organism | Ia | II | III | IV | V | VI | VII |
| *Staphylococcus aureus,* beta-lactamase negative | | | | | | | |
| SSC 79-3 | .12 | .5 | 1 | 1 | 2 | 2 | .5 |
| SSC 79-5 | .5 | 1 | 4 | 1 | 8 | 2 | 2 |
| SSC 79-7 | .12 | .5 | 1 | .5 | 2 | 1 | .5 |
| SSC 79-9 | .12 | .5 | 2 | 1 | 2 | 1 | .5 |
| SSC 79-10 | .12 | .5 | 1 | 1 | 2 | 1 | .5 |
| SSC 79-11 | .12 | .5 | 1 | .5 | 2 | 1 | .25 |
| SSC 79-17 | .25 | 1 | 2 | 1 | 4 | 2 | 1 |
| SSC 79-14 | .5 | 2 | 4 | 4 | 4 | 2 | 2 |
| SSC 79-15 | .5 | 2 | 4 | 1 | 8 | 4 | 2 |
| *Staphyllococcus aureus,* beta-lactamase positive | | | | | | | |
| SSC 79-27 | .25 | 1 | 2 | .5 | 4 | 2 | 1 |
| SSC 79-28 | .25 | 1 | 2 | .5 | 4 | 2 | 2 |
| SSC 79-36 | .25 | 1 | 2 | 1 | 4 | 2 | 2 |
| SSC 79-38 | .25 | 1 | 2 | .5 | 2 | 2 | 1 |
| SSC 79-39 | .25 | 1 | 4 | 4 | 4 | 4 | 2 |
| SSC 79-41 | .5 | 2 | 4 | 1 | 4 | 4 | 2 |
| SSC 79-44 | .12 | 1 | 2 | .5 | 2 | 2 | 1 |
| SSC 79-47 | .25 | 1 | 2 | 1 | 4 | 2 | 2 |
| SSC 79-24 | 4 | 16 | 32 | >128 | 32 | 16 | 128 |

In Table III the compounds are identified as follows:
Compound Ib(i): 7-$\beta$-[$\alpha$-syn-methoxyimino-$\alpha$-(2-aminothiazol-4-yl)acetamido]-3-[(1,2,3-thiadiazol-4-methyl-5-ylthio)methyl]-3-cephem-4-carboxylic acid
Compound II: Cephalothin (Lilly)

TABLE III

| | | Minimal Inhibitory Concentration mcg/ml Compound | |
|---|---|---|---|
| Organism | | Ib(i) | II |
| Klebsiella pneumoniae | STFD-79-6 | ≦.03 | .5 |
| Klebsiella pneumoniae | SSC-78-1 | ≦.03 | 1 |
| Klebsiella pneumoniae | AD | ≦.03 | .03 |
| Enterobacter aerogenes | STFD-79-14 | .12 | >128 |
| Enterobacter cloacae | K-79-16 | .25 | >128 |
| Serratia marcescens | TUL-78-15 | 2 | >128 |
| Serratia marcescens | QHC-77-2 | 2 | >128 |
| Proteus morganii | K-79-25 | ≦.03 | >128 |
| Proteus rettgeri | N-76-1 | ≦.03 | >128 |
| Escherichia coli | STFD-79-20 | ≦.03 | 2 |
| Escherichia coli | #311 | .06 | 4 |
| Escherichia coli | ESS 22-31 | ≦.03 | ≦.03 |
| Escherichia coli | ATCC 25922 | ≦.03 | 2 |
| Salmonella sp. | SSC-79-57 | 1 | 64 |
| Salmonella sp. (arizona) | QHC-77-3 | .06 | 2 |
| Acinetobacter sp. | STFD-79-17 | 32 | >128 |
| Acinetobacter sp. | K-77-1 | 4 | >128 |
| Pseudomonas aeruginosa | SSC-78-13 | 64 | >128 |
| Pseudomonas aeruginosa | 12-4-4 | 64 | >128 |
| Pseudomonas aeruginosa | ATCC 27853 | 64 | >128 |
| Enterococcus sp. | OSU-75-1 | 8 | 16 |
| Enterococcus sp. | SM-77-15 | 8 | 16 |
| Staphylococcus aureus | SSC-79-18 | .25 | .12 |
| Staphylococcus aureus | FU-79-19-2 | .5 | .12 |
| Staphylococcus aureus | Smith | .25 | .03 |
| Staphylococcus aureus | SSC-80-15 | 1 | .5 |
| Micrococcus luteus | PCI 1001 | ≦.03 | .03 |

The usefulness of these new compounds is further demonstrated by their ability to control systemic lethal infections in mice. The test employed used Charles River Laboratories CD-1 strain female mice each weighing 20+2 grams. The mice were infected by intraperitoneal injection of sufficient bacteria (see Table 2), contained in either 0.5 ml. of 5% mucin (*S. aureus* strains) or broth (*S. pyogenes* or *E. coli*), to kill 95–100% of untreated mice within 48 hours.

The mice were treated by subcutaneous injection 30 minutes after infection with the test drug at varying doses contained in 0.5 ml. of 0.2% aqueous agar. Survival ratios seven days after infection were recorded. The results of three separate tests on Compound Ia were pooled and appear in Table IV as median effective doses ($ED_{50}$'s) which were determined by probit analysis.

The compounds in Table IV are coded as follows:
Compound Ia = 7 beta-[alpha-syn-methoxyimino-alpha-(2-aminothiazol-4-yl)acetamido]-3-[(1,2,3-thiadiazol-5-ylthio)methyl]-3-cephem-4-carboxylic acid

TABLE IV

| Infecting Bacteria | | Median Effective Dose ($ED_{50}$) mg/kg (95% confidence limits) Compound Ia |
|---|---|---|
| *Staphylococcus aureus* | Smith | 2.9 (2.4–3.6) |
| *Staphylococcus aureus* | Fu-79-2 | 6.1 (4.4–8.4) |
| *Staphylococcus pyogenes* | C 203 | 0.1 (0.08–0.13) |
| *Escherichia coli* | 311 | 0.35 (0.28–0.44) |

The active compounds of the present invention are effective in treating bacterial infections in warm-blooded animals when administered parenterally in amounts ranging from about 15 mg. to about 200 mg. per kilogram of body weight per day. A preferred dosage range is from about 20 mg. to about 60 mg. per kilogram of body weight per day. A preferred dosage unit contains about 15 mg. to about 2 g. of the active compound. A more preferred dosage unit contains about 50 mg. to about 1 g. of active compound. Dosage units are regulated so that a total of approximately 4–12 g. of the active compounds is administered in a 24-hour period for a subject of about 70 kg. of body weight. This dosage regimen may be adjusted to provide for the optimum therapeutic response. For example, a preferred dosage regimen for non-life-threatening infections is approximately 15–200 mg. per kilogram of body weight per day; for serious or life-threatening infections the dosage can be increased up to 350 mg. per kg. of body weight per day. Several divided doses may be administered daily, or the dosage may be proportionally reduced as indicated by the exigencies of the therapeutic situation.

These active compounds may be administered by many convenient methods, as for example by the intravenous, intramuscular, subcutaneous, or intraperitoneal routes.

Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injection include sterile aqueous solutions or dispersions and sterile injectable solutions or dispersions. In all cases, the form must be sterile and must be sufficiently fluid to facilitate the use of a hypodermic syringe. It must be stable under the conditions of manufacture and storage and must be preserved against contamination by microorganisms such as bacteria and fungi. The carrier may be a solvent or dispersion medium containing, for example, water, ethanol, polyol (e.g. glycerol, propylene glycol and liquid polyethylene glycol), suitable mixtures thereof, and vegetable oils.

A further understanding of the invention can be had from the following non-limiting Preparations and Examples. As used hereinabove and below unless expressly stated to the contrary, all temperatures and temperature ranges refer to the centigrade system and the terms ambient or room temperature refer to about 20° C. The term percent or (%) refers to weight percent and the terms mole and moles refer to gram moles. The term equivalent refers to a quantity of reagent equal in moles to the moles of the preceding or succeeding reactant recited in that preparation or example in the terms of moles of finite weight or volume.

EXAMPLE 1

7β-[α-syn-Methoxyimino-α-(2-aminothiazol-4-yl)acetamido]-3-[(1,2,3-thiadiazol-5-ylthio)methyl]-3-cephem-4-carboxylic acid A solution of 245 mg. of the sodium salt of 7β-[α-syn-methoxyimino-α-(2-aminothiazol-4-yl)acetamido]-cephalosporanic acid and 78 mg. of the potassium salt of 1,2,3-thiadiazol-5-thiol in 5 ml. of water is heated at 65° C. at pH 7.3 for 6 hours. The solution is extracted with ethyl acetate and adjusted to pH 2.5 with 1 N hydrochloric acid. The precipitate which forms is recovered by filtration, giving 70 mg. of the desired product as a tan solid, $\lambda_{max}^{KBr}$ 5.62 (β-lactam carbonyl).

EXAMPLE 2

7β-[α-syn-Methoxyimino-α-(2-aminothiazol-4-yl)acetamido]-3-[(1,2,3-thiadiazol-5-ylthio)methyl]-3-cephem-4-carboxylic acid A 3.17 g. portion of dicyclohexylcarbodiimide is added to a solution of 13.0 g. of 2-(2-tritylamino-4-thiazolyl)-2-syn-methoxyiminoacetic acid in 60 ml. of methylene chloride. The mixture is stirred in the cold for 30 minutes and then at room temperature for 1.5 hours. The urea is removed by filtration, the filtrate is chilled in an ice/methanol bath and a cold solution of 4.4 g. of 7-amino-3-(1,2,3-thiadiazol-5-yl)thiomethyl-3-cephem-4-carboxylic acid and 3.72 ml. of triethylamine in 60 ml. of methylene chloride is added. This mixture is stirred in the cold for 30 minutes and then at room temperature overnight. The reaction mixture is extracted in succession with cold 0.5 N hydrochloric acid, water and brine, then dried over magnesium sulfate. Evaporation of the solvent gives an oil which is dissolved in a solution of 30 ml. of dioxane and 30 ml. of ether. A 2.92 ml. portion of diethylamine is added and the solution is chilled and filtered giving as a by-product 6.2 g. of the diethylammonium salt of 2-(2-tritylamino-4-thiazolyl)-2-syn-methoxyiminoacetic acid. The filtrate is diluted to 500 ml. with ether, chilled and filtered, giving 8.5 g. of 7-[2-(2-tritylamino-4-thiazolyl)-2-syn-(methoxyimino)acetamido]-3-(1,2,3-thiadiazol-5-yl)thiomethyl-3-cephem-4-carboxylic acid as the diethylammonium salt.

A mixture of 2.4 g. of the above diethylammonium salt and 20 ml. of 80% formic acid is stirred at room temperature for 2 hours, then diluted with 20 ml. of water and filtered. The filtrate is evaporated to dryness at 35° C. and the residue is triturated with ether, filtered and dried, giving 1.4 g. of the desired product.

EXAMPLE 3

Sodium 7β-[α-syn-methoxyimino-α-(2-aminothiazol-4-yl)acetamido]-3-[(1,2,3-thiadiazol-5-ylthio)methyl]-3-cephem-4-carboxylate A 3.5 g. portion of 7β-[α-syn-methoxyimino-α-(2-aminothiazol-4-yl)acetamido]-3-[(1,2,3-thiadiazol-5-ylthio)methyl]-3-cephem-4-carboxylic acid is dissolved in 100 ml. of water by the dropwise addition of 6.6 ml. of 1 N sodium hydroxide. This solution is filtered and the filtrate lyophilized, giving 3.3 g. of the desired product.

EXAMPLE 4

7-Amino-3-[(1,2,3-thiadiazol-4-methyl-5ylthio)methyl]-3-cephem-4-carboxylic acid A mixture of 4.04 g. of 7-aminocephalosporanic acid, 2.30 g. of sodium 4-methyl-1,2,3-thiadiazol-5-thiolate and 1.24 g. of sodium bicarbonate in 60 ml. of water and 30 ml. of acetone is stirred and refluxed for 2.5 hours. The reaction mixture is cooled to room temperature, acidified to pH 3.5 and the precipitate collected, washed with water and dried, giving 3.7 g. of the desired compound.

EXAMPLE 5

7β-[α-syn-Methoxyimino-α-(2-tritylamino-thiazol-4-yl)acetamido]-3-[(1,2,3-thiadiazol-4-methyl-5-ylthio)methyl]-3-cephem-4-carboxylic acid A 2.08 g. portion of phosphorous pentachloride is added in several portions to a cold solution of 4.44 g. of 2-(2-tritylamino-4-thiazolyl-2-syn-methoxyiminoacetic acid and 1.41 ml. of triethylamine in 70 ml. of methylene chloride. This mixture is stirred in the cold for 30 minutes and then at room temperature for 30 minutes. The solvent is removed at reduced pressure. The residue is dissolved in 70 ml. of methylene chloride and again evaporated to dryness. This residue is slurried in 50 ml. of acetone, filtered and the filtrate is added dropwise, with stirring to a cold solution of 2.53 g. of 7-amino-3-[(1,2,3-thiadiazol-4-methyl-5-ylthio)methyl]-3-cephem-4-carboxylic acid, 0.84 g. of sodium bicarbonate and 2.82 ml. of triethylamine in 75 ml. of water containing 50 ml. of acetone. This mixture is stirred in the cold for 30 minutes, then at room temperature for one hour and acidified to pH 2. A 100 ml. portion of water is added and the mixture is extracted with three 150 ml. portions of ethyl acetate. The combined ethyl acetate extracts are washed with water and brine, then dried over magnesium sulfate and evaporated, giving 6.3 g. of the desired compound.

EXAMPLE 6

7β-[α-syn-Methoxyimino-α-(2-aminothiazol-4-yl)acetamido]-3-[(1,2,3-thiadiazol-4-methyl-5-ylthio)methyl]-3-cephem-4-carboxylic acid A 4.0 g. portion of 7-β-[α-syn-methoxyimino-α-(2-tritylaminothiazol-4-yl)acetamido]-3-[(1,2,3-thiadiazol-4-methyl-5-ylthio)methyl]-3-cephem-4-carboxylic acid is added to 40 ml. of 80% formic acid and the mixture is stirred at room temperature for 2.5 hours. A 40 ml. portion of water is added, the mixture is filtered and the filtrate evaporated to dryness at 35° C. The residue is triturated with water, filtered and dried, giving 1.7 g. of the desired product.

EXAMPLE 7

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 8

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 9

Preparation of Intramuscular Product

A 268 liter portion of sterile water for injection USP is placed in a mixing tank and chilled to 6° C.±4° C. A 70,219 g. portion of 7β-[α-syn-methoxyimino-α-(2-aminothiazol-4-yl)acetamido]-3-(1,2,3-thiadiazol-5-ylthio)methyl)-3-cephem-4-carboxylic acid is suspended in the water and 11,016 g, of sodium bicarbonate are added in about ten equal portions. The solution at 6° C.±4° C. is mixed for 3–5 hours and then diluted to 535 liters with sterile water for injection USP at the same temperature. The solution is then sterile filtered, filled in sterile glass vials at 50.56 ml. per vial and lyophilized. Reconstitution with 11.6 ml. of suitable diluent such as sterile water for injection USP yields 15.8 ml. of product at a concentration of 400 mg./ml. as the sodium salt.

EXAMPLE 10

Preparation of Intravenous Product

The procedure of the example for the intramuscular product is repeated. The vials are filled at 48.0 ml. and lyophilized. Reconstitution is with 5 ml. of suitable diluent which is then further diluted to 50 ml. (or desired volume) providing a 6 g. infusion.

We claim:

1. A compound selected from those of the formula:

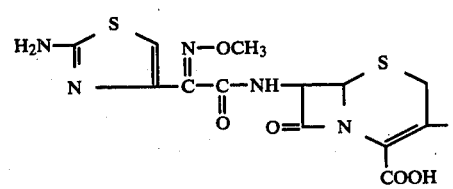

-continued

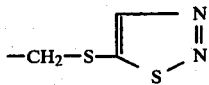

wherein R is selected from the group consisting of hydrogen and $R_1$, wherein $R_1$ is $C_1$–$C_6$ alkyl; and the pharmaceutically acceptable nontoxic cation salts thereof.

2. The compound of claim 1, 7β-[α-syn-methoxyimino-α-(2-aminothiazol-4-yl)acetamido]-3-[(1,2,3-thiadiazol-5-ylthio)methyl]-3-cephem-4-carboxylic acid.

3. The compound of claim 1, 7β-[α-syn-methoxyimino-α-(2-aminothiazol-4-yl)acetamido]-3-[(1,2,3-thiadiazol-4-methyl-5-ylthio)methyl]-3-cephem-4-carboxylic acid.

4. A method for treating bacterial infections in warm-blooded animals which comprises administering to said animals an effective amount of a compound selected from those of the formula:

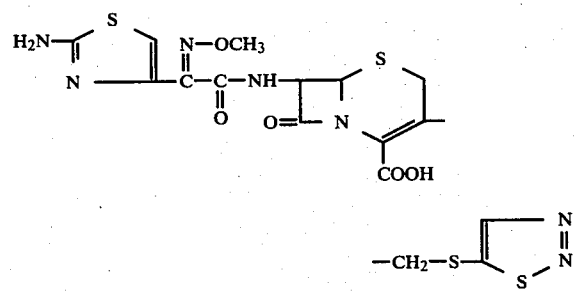

wherein R is selected from the group consisting of hydrogen and $R_1$, wherein $R_1$ is $C_1$–$C_6$ alkyl; and the pharmaceutically acceptable nontoxic cationic salts thereof.

5. The method in accordance with claim 4, wherein the compound is 7β-[α-syn-methoxyimino-α-(2-aminothiazol-4-yl)acetamido]-3-[(1,2,3-thiadiazol-5-ylthio)-methyl]-3-cephem-4-carboxylic acid.

6. The method in accordance with claim 4, wherein the compound is 7β-[α-syn-methoxyimino-α-(2-aminothiazol-4-yl)acetamido]-3-[(1,2,3-thiadiazol-4-methyl-5-ylthio)methyl]-3-cephem-4-carboxylic acid.

7. A composition of matter which comprises an effective amount of a compound of the formula:

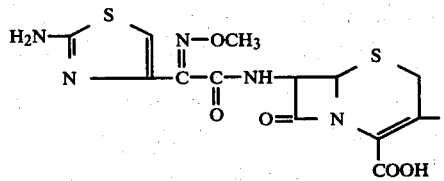

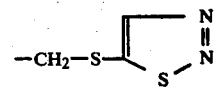

wherein R is selected from the group consisting of hydrogen and $R_1$ wherein $R_1$ and $C_1$–$C_6$ alkyl, and the pharmaceutically acceptable nontoxic cationic salts thereof, in association with a pharmaceutically acceptable carrier.

8. The composition of matter in accordance with claim 7, wherein the compound is 7β-[α-syn-methoxyimino-α(2-aminothiazol-4-yl)acetamido]-3-[(1,2,3-thiadiazol-5-ylthio)methyl]-3-cephem-4-carboxylic acid.

9. The composition of matter in accordance with claim 7, wherein the compound is 7β-[α-syn-methoxyimino-α-2-aminothiazol-4-yl)acetamido]-3-[(1,2,3-thiadiazol-4-methyl-5-ylthio)methyl]-3-cephem-4-carboxylic acid.

* * * * *

UNITED STATES PATENT OFFICE
CERTIFICATE OF CORRECTION

Patent No. 4,399,132     Dated August 16, 1983

Inventor(s) WILLIAM V. CURRAN and ADMA S. ROSS

It is certified that error appears in the above-identified patent and that said Letters Patent are hereby corrected as shown below:

Claim 1, Col. 15, Line 2 should read:

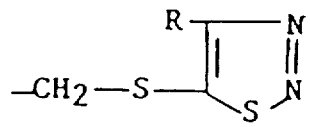

Claim 4, Col. 15, Line 31 should read:

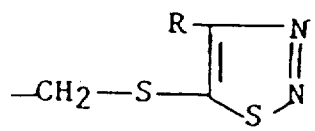

UNITED STATES PATENT OFFICE
CERTIFICATE OF CORRECTION

Patent No. 4,399,132              Dated August 16, 1983

Inventor(s) WILLIAM V. CURRAN and ADMA S. ROSS

It is certified that error appears in the above-identified patent and that said Letters Patent are hereby corrected as shown below:

Claim 7, Col. 16, Line 18, should read:

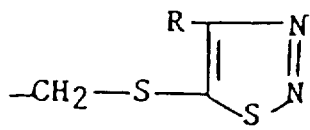

Signed and Sealed this

Twenty-eighth Day of May 1985

[SEAL]

Attest:

DONALD J. QUIGG

Attesting Officer    Acting Commissioner of Patents and Trademarks